United States Patent
Ogasawara

(10) Patent No.: US 9,492,330 B2
(45) Date of Patent: Nov. 15, 2016

(54) MANUFACTURING METHOD AND A MANUFACTURING APPARATUS FOR A SHEET-LIKE MEMBER ASSOCIATED WITH AN ABSORBENT ARTICLE

(75) Inventor: Yoshikazu Ogasawara, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 602 days.

(21) Appl. No.: 13/394,847

(22) PCT Filed: Sep. 10, 2010

(86) PCT No.: PCT/JP2010/065582
§ 371 (c)(1),
(2), (4) Date: May 4, 2012

(87) PCT Pub. No.: WO2011/033996
PCT Pub. Date: Mar. 24, 2011

(65) Prior Publication Data
US 2012/0225764 A1    Sep. 6, 2012

(30) Foreign Application Priority Data
Sep. 18, 2009 (JP) .................. 2009-217911

(51) Int. Cl.
*B31B 1/26* (2006.01)
*A61F 13/15* (2006.01)

(52) U.S. Cl.
CPC ... *A61F 13/15756* (2013.01); *A61F 13/15747* (2013.01); *A61F 13/15764* (2013.01); *A61F 13/15804* (2013.01)

(58) Field of Classification Search
CPC ................... A61F 13/15804; A61F 13/15764; A61F 13/49; A61F 13/496; A61F
(Continued)

(56) References Cited

U.S. PATENT DOCUMENTS 3,430,629 A * 3/1969 Murphy ............ A61F 13/49426
604/372
3,557,156 A   1/1971 Enneper et al.
(Continued)

FOREIGN PATENT DOCUMENTS

JP        9267971 A   10/1997
JP     2004121761 A    4/2004
(Continued)

OTHER PUBLICATIONS

Office Action received Jul. 22, 2014, corresponds to Egyptian patent application No. 2012030473.
(Continued)

*Primary Examiner* — Michelle Lopez
*Assistant Examiner* — Chinyere Rushing-Tucker
(74) *Attorney, Agent, or Firm* — Hauptman Ham, LLP

(57) ABSTRACT

There is provided a manufacturing method for a sheet-like member associated with an absorbent article, the sheet-like member having a folded-up section which is temporarily-secured in a folded-up state. The method includes: forming the folded-up section by folding up a continuous sheet in a width direction of the continuous sheet, the continuous sheet continuing along a transporting direction, creasing the folded-up section in a folded-up state by pressing continuously the folded-up section along a direction of a fold line of the folded-up section, temporarily-securing the folded-up section in a folded-up state by pressing the folded-up section with a plurality of protrusions that are included in a pressing member, producing the sheet-like member by dividing the continuous sheet with a predetermined pitch in the transporting direction, the continuous sheet having been creased and temporarily-secured, and conveying the produced sheet-like member.

11 Claims, 9 Drawing Sheets

(58) Field of Classification Search
CPC .............. 13/4963;A61F 13/49001; A61F 13/4704; A61F 13/15707; A61F 13/15731; A61F 13/15577; A61F 13/15747; A61F 13/15756
USPC ............... 493/405, 424, 427, 434, 435, 442
See application file for complete search history.

(56) References Cited

U.S. PATENT DOCUMENTS

| | | | |
|---|---|---|---|
| 2005/0087292 A1* | 4/2005 | McFall | A61F 13/15699 156/290 |
| 2010/0065199 A1 | 3/2010 | Hormung et al. | |
| 2010/0201024 A1* | 8/2010 | Gibson | B26F 1/20 264/156 |
| 2010/0331799 A1* | 12/2010 | Schneider | A61F 13/15707 604/358 |
| 2011/0173794 A1* | 7/2011 | Sakaguchi | A61F 13/15756 29/428 |
| 2011/0277921 A1* | 11/2011 | Ogasawara | A61F 13/15804 156/226 |
| 2012/0208688 A1* | 8/2012 | Sakaguchi | A61F 13/15804 493/343 |
| 2013/0060222 A1* | 3/2013 | Gerstle | A61F 13/15747 53/429 |
| 2015/0119843 A1* | 4/2015 | Kurihara | A61F 13/51104 493/374 |

FOREIGN PATENT DOCUMENTS

| | | | | |
|---|---|---|---|---|
| JP | 2004141627 A | 5/2004 | | |
| JP | 2004298455 A | 10/2004 | | |
| JP | 2005-218648 A | 8/2005 | | |
| JP | 2005312707 A | 11/2005 | | |
| JP | 2006340978 A | 12/2006 | | |
| JP | 2007202691 A | 8/2007 | | |
| JP | 2009195303 A | 9/2009 | | |
| WO | 2008141834 A1 | 11/2008 | | |
| WO | 2009123213 A1 | 10/2009 | | |
| WO | WO 2009123176 A1 * | 10/2009 | ....... | A61F 13/15756 |
| WO | WO 2009123178 A1 * | 10/2009 | ....... | A61F 13/15756 |
| WO | WO 2010071023 A1 * | 6/2010 | ....... | A61F 13/15723 |
| WO | 2010101283 A1 | 9/2010 | | |

OTHER PUBLICATIONS

Office Action issued Feb. 24, 2015, corresponds to Egyptian patent application No. 2012030473.
Supplementary European Search Report issued Feb. 28, 2014, corresponds to European patent application No. 10817109.1.
Corresponding Japanese Application No. 2009-217911 Office Action dated Jun. 19, 2013.
International Search Report for PCT/JP2010/065582 dated Nov. 30, 2010.
Office Action mailed Jun. 18, 2015, corresponding to European patent application No. 10817109.1.

* cited by examiner

B-B CROSS SECTION

C-C CROSS SECTION

MANUFACTURING METHOD AND A MANUFACTURING APPARATUS FOR A SHEET-LIKE MEMBER ASSOCIATED WITH AN ABSORBENT ARTICLE

RELATED APPLICATIONS

The present application is a National Phase of International Application Number PCT/JP2010/065582, filed Sep. 10, 2010, and claims priority from, Japanese Application Number 2009-217911, filed Sep. 18, 2009.

TECHNICAL FIELD

The invention relates to a manufacturing method and a manufacturing apparatus for a sheet-like member associated with an absorbent article such as disposable diaper etc.

BACKGROUND ART

Disposable diapers are known as a conventional absorbent article to absorb exudates. In a manufacturing line for these diapers, while a half-completed product of the diaper is being conveyed, various components of the diaper are attached to the half-completed product in a sequence by joining, etc and the diaper is finished. One of these components is, for example, a sheet-like member including folded-up sections which are folded up so as to be opened and closed. The folded-up sections are opened for use when a diaper is used.

However, if the folded-up sections of the sheet-like member open up because of air resistance, etc while being conveyed in the manufacturing line, it may cause some problems such as being entrapped by devices around the conveying path. Therefore, in the manufacturing line, the folded-up sections are temporarily secured in a folded-up state by embossing them. That is, by pressing the folded-up sections with a plurality of protrusions of an embossing roll, the surfaces of the folded-up section which are to overlay each other are intermittently crimped, and thereby the folded-up sections are temporarily secured in a folded-up state (see [PTL 1]).

CITATION LIST

Patent Literature

[PTL 1] Japanese Patent Application Laid-open Publication No. 2007-202691

SUMMARY OF THE INVENTION

Technical Problem

However, in some cases, the temporary-securing by the foregoing intermittent crimping may not be sufficient. For example, it is possible that a gap is produced in a portion of the foregoing surfaces which overlay each other but are not crimped. In particular, in the peripheral portion of the fold line of the folded-up section, a force for recovery from the folding is large, and therefore, a gap is likely to be produced. When a gap is produced, air resistance during conveying acts in the direction that will open the gap, and this may cause the temporarily-secured surfaces to easily separate starting from the gap.

Further, the folded-up section is generally thick because of the folds. The thickness leads to a greater air resistance being encountered while being conveyed; the air resistance tends to encourage the opening up of the folded-up section. Therefore, the temporarily-secured surfaces become likely to separate.

The invention has been made in view of the above conventional problems, and an advantage thereof is to provided a manufacturing method and a manufacturing apparatus for a sheet-like member associated with an absorbent article in which, while conveying the sheet-like member including a folded-up section which is temporarily secured in a folded-up state, the folded-up section can be reliably maintained in the folded-up state.

Solution to Problem

An aspect of the invention to achieve the above advantage is
a manufacturing method for a sheet-like member associated with an absorbent article, the sheet-like member having a folded-up section which is temporarily-secured in a folded-up state, including:
forming the folded-up section by folding up a continuous sheet in a width direction of the continuous sheet, the continuous sheet continuing along a transporting direction,
creasing the folded-up section in a folded-up state by pressing continuously the folded-up section along a direction of a fold line of the folded-up section,
temporarily-securing the folded-up section in a folded-up state by pressing the folded-up section with a plurality of protrusions that are included in a pressing member,
producing the sheet-like member by dividing the continuous sheet with a predetermined pitch in the transporting direction, the continuous sheet having been creased and temporarily-secured, and
conveying the produced sheet-like member.
Further,
a manufacturing apparatus for a sheet-like member associated with an absorbent article, the sheet-like member having a folded-up section which is temporarily-secured in a folded-up state, including:
a first unit that forms the folded-up section by folding up a continuous sheet in a width direction of the continuous sheet, the continuous sheet continuing along a transporting direction;
a second unit that, by pressing continuously the folded-up section along a direction of a fold line of the folded-up section, creases the folded-up section in a folded-up state;
a third unit that temporarily-secures the folded-up section in a folded-up state by pressing the folded-up section with a plurality of protrusions that are included in a pressing member;
a fourth unit that produces the sheet-like member by dividing the continuous sheet with a predetermined pitch in the transporting direction, the continuous sheet having been creased and temporarily-secured; and
a fifth unit that conveys the produced sheet-like member.

Other features of this invention will become apparent from the description in this specification and the attached drawings.

Effects of the Invention

According to the invention, while conveying a sheet-like member including a folded-up section which is temporarily secured in a folded-up state, the folded-up section can be reliably maintained in the folded-up state.

MODE FOR CARRYING OUT THE INVENTION

Figure 1A:
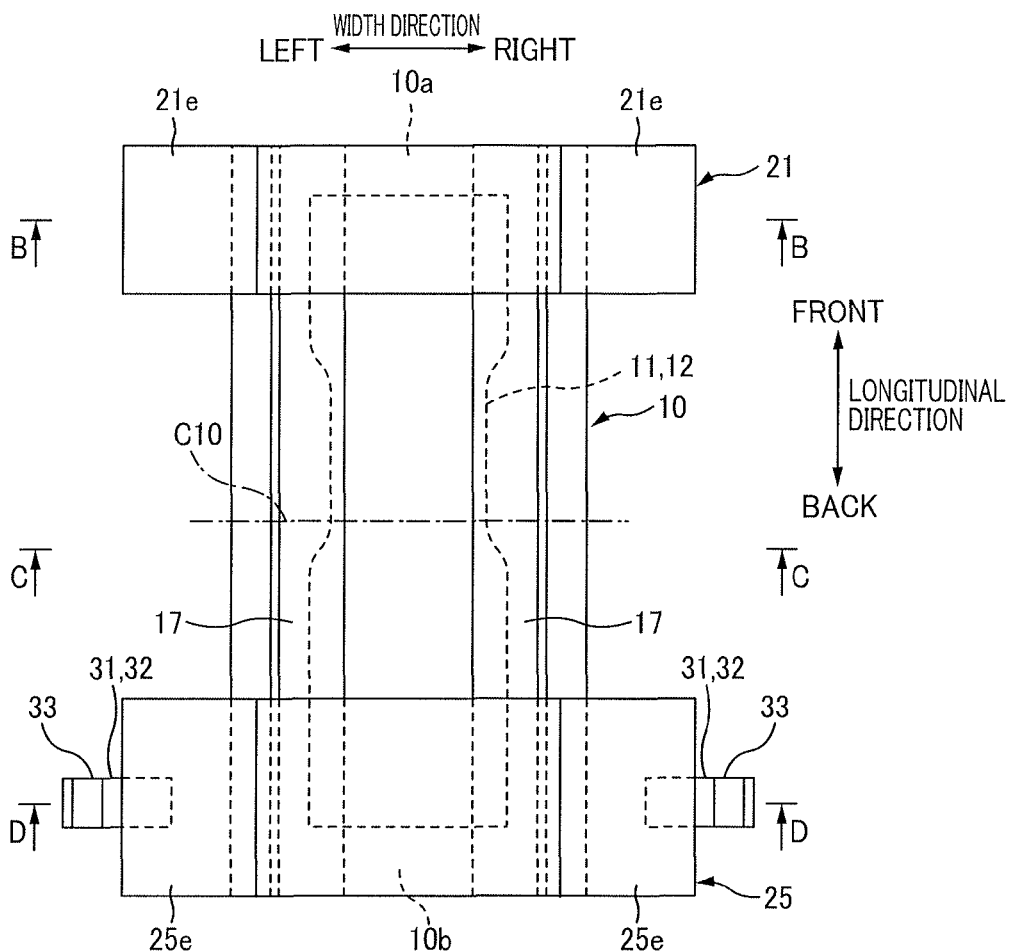
FIG. 1A is a plan view of a disposable diaper 1 in its opened condition.

At least the following matters will be made clear by the description in the present specification and the accompanying drawings.

A manufacturing method for a sheet-like member associated with an absorbent article, the sheet-like member having a folded-up section which is temporarily-secured in a folded-up state, including:
  forming the folded-up section by folding up a continuous sheet in a width direction of the continuous sheet, the continuous sheet continuing along a transporting direction,
  creasing the folded-up section in a folded-up state by pressing continuously the folded-up section along a direction of a fold line of the folded-up section,
  temporarily-securing the folded-up section in a folded-up state by pressing the folded-up section with a plurality of protrusions that are included in a pressing member,
  producing the sheet-like member by dividing the continuous sheet with a predetermined pitch in the transporting direction, the continuous sheet having been creased and temporarily-secured, and
  conveying the produced sheet-like member.

With such a manufacturing method for a sheet-like member associated with an absorbent article, in addition to temporarily-securing, the folded-up section is continuously pressed along the direction of the fold line of the folded-up section. Thereby, the folded-up section is creased in a folded-up state along the entire length thereof in that direction. That is, the folded-up section is continuously pressed along the direction of the fold line. Therefore, the surfaces of the folded-up section which are to overlay each other are more likely to come into close contact along the entire length thereof in that direction. This effectively prevents a gap from being produced between these surfaces along the entire length thereof in that direction. As a result, in "conveying the sheet-like member" which is a subsequent process, when the folded-up section encounters air resistance, the folded-up section in which a gap is suppressed is less likely to be opened up. This enables the sheet-like member to be reliably maintained in a folded-up state while being conveying.

Further, the creasing of the folded-up section along the entire length thereof in that direction decreases considerably the force of the peripheral portion of the fold line for recovery from the folding. The peripheral portion of the fold line becomes less likely to open up. That is, producing a gap is greatly suppressed in the peripheral portion of the fold line.

Further, the folded-up section is continuously pressed along the direction of the fold line. Therefore, the thickness of the folded-up section becomes smaller. As a result, the folded-up section is less likely to encounter air resistance while being conveyed.

In such a manufacturing method for a sheet-like member associated with absorbent article, it is desirable that
  in the creasing,
    in passing the continuous sheet through a nip between a pair of creasing rolls that rotate with their outer circumferential surfaces facing each other, the outer circumferential surface of the pair of creasing rolls continuously presses the folded-up section along the direction of the fold line,
  in the temporarily-securing,
    the pressing member includes
      an embossing roll that rotates and has a plurality of protrusions on an outer circumferential surface thereof and
      a roll that rotates with its outer circumferential surface facing the embossing roll, and
    in passing the continuous sheet through a nip between the embossing roll and the roll, the protrusions and the outer circumferential surface press the folded-up section.

With such a manufacturing method for a sheet-like member associated with an absorbent article, the creasing roll and the embossing roll are used. Therefore, both creasing and temporary-securing of the folded-up section of the continuous sheet in a folded-up state can be stable in the transporting direction of the continuous sheet.

In such a manufacturing method for a sheet-like member associated with absorbent article, it is desirable that
  the embossing roll and the roll also function as the pair of creasing rolls, and
  concerning creasing the folded-up section in a folded-up state, by constantly pressing the folded-up section with either of the protrusion of the embossing roll and a portion surrounding the protrusion, the folded-up section is continuously pressed along the direction of the fold line.

With such a manufacturing method for a sheet-like member associated with an absorbent article, the number of rolls can be reduced in half, which results in simplifying the configuration of the apparatus or reducing costs.

Further, in the foregoing manufacturing method, the temporary-securing by the protrusions and the creasing are both performed substantially simultaneously. Therefore, both of these steps can be performed reliably. The detail is as follows.

For example, if temporarily-securing the folded-up section of the continuous sheet prior to creasing, it is possible that when the pair of creasing rolls press the folded-up section the temporarily-secured surfaces of the folded-up section separate. On the other hand, in the case of creasing prior to temporarily-securing, it is possible that when pressed by the protrusions of the embossing roll the surfaces of the folded-up section which overlay in close contact with each other by creasing separate unintentionally, resulting in a gap between the surfaces. That is, regardless of the sequence of the two steps, problems may be caused. However, if, as mentioned above, the embossing roll and the roll also function as the pair of creasing rolls, the temporary-securing by the protrusions and the creasing are both performed substantially simultaneously. Therefore, these problems can be avoided; thereby, both of these steps can be performed reliably.

In such a manufacturing method for a sheet-like member associated with absorbent article, it is desirable that
  in the forming of the folded-up section, a pair of the folded-up sections are formed by folding up inwardly in the width direction both end sections of the continuous sheet in the width direction,
  on the outer circumferential surface of the embossing roll, a protrusion group consisting of the plurality of protrusions is placed corresponding to the folded-up section, the plurality of protrusions being arranged along an entire length in a circumferential direction of the embossing roll,
  the protrusion group is defined to have a predetermined width in a direction along a rotational axis of the embossing roll, and
  the predetermined width of the protrusion group is set to be greater than a width of the folded-up section.

With such a manufacturing method for a sheet-like member associated with an absorbent article, even if the continuous sheet which is being conveyed in the transporting direction is somewhat meandering in the width direction, the folded-up section of the continuous sheet can be temporarily-secured reliably.

In such a manufacturing method for a sheet-like member associated with absorbent article, it is desirable that
  in the forming of the folded-up section, a pair of the folded-up sections are formed by folding up inwardly in the width direction both end sections of the continuous sheet in the width direction,
  on the outer circumferential surface of the pair of creasing rolls, a pressing region that presses the folded-up section is defined along an entire length in a circumferential direction of the creasing rolls, the pressing region corresponding to the folded-up section and having a predetermined width in a direction along a rotational axis of the creasing roll, and
  the predetermined width associated with the pressing region is set to be greater than a width of the folded-up section.

With such a manufacturing method for a sheet-like member associated with an absorbent article, even if the continuous sheet which is being conveyed in the transporting direction is somewhat meandering in the width direction, the folded-up section of the continuous sheet can be creased reliably.

In such a manufacturing method for a sheet-like member associated with an absorbent article, it is desirable that
  while being folded inwardly in the width direction, both end sections of the continuous sheet in the width direction are each fixed with an adhesive and a pair of folded sections are formed,
  in the forming of the folded-up section, by folding up each of the pair of folded sections more inwardly in the width direction, the folded-up section is formed, and
  the forming, the creasing, and the temporary-securing of the folded-up section are performed before the adhesive on the folded section loses its fluidity.

With such a manufacturing method for a sheet-like member associated with an absorbent article, when pressing for the aforementioned "creasing" and "temporarily-securing," the adhesive which is used for fixing the folded section soaks through and in between the surfaces of the folded-up section which are to overlay each other. As a result, the adhesive not only assists in the aforementioned temporarily-secured contact, but also removes the wrinkles of the folded-up section as happens with sized fabric, resulting in prevention of producing the gap between the surfaces. This enables the folded-up section to be more reliably maintained in a folded-up state.

In such a manufacturing method for a sheet-like member associated with an absorbent article, it is desirable that
  the continuous sheet is made mainly of a thermoplastic resin fiber, and
  outer circumferential surfaces of a pair of creasing rolls are heated by a heating device.

With such a manufacturing method for a sheet-like member associated with an absorbent article, the pair of creasing rolls press the folded-up section with the continuous sheet being heated and plasticized. Therefore, the folded-up section can be more reliably creased.

Further,
  a manufacturing apparatus for a sheet-like member associated with an absorbent article, the sheet-like member having a folded-up section which is temporarily-secured in a folded-up state, including:
    a first unit that forms the folded-up section by folding up a continuous sheet in a width direction of the continuous sheet, the continuous sheet continuing along a transporting direction;
    a second unit that, by pressing continuously the folded-up section along a direction of a fold line of the folded-up section, creases the folded-up section in a folded-up state;
    a third unit that temporarily-secures the folded-up section in a folded-up state by pressing the folded-up section with a plurality of protrusions that are included in a pressing member;
    a fourth unit that produces the sheet-like member by dividing the continuous sheet with a predetermined pitch in the transporting direction, the continuous sheet having been creased and temporary-secured; and
    a fifth unit that conveys the produced sheet-like member.

With such a manufacturing apparatus for a sheet-like member associated with an absorbent article, the same effect as the foregoing manufacturing method can be achieved.

===Present Embodiment===

In a manufacturing method for a sheet-like member associated with an absorbent article according to the present embodiment, parts of a disposable diaper 1 are manufactured; that is, the band-member intermediate part 20 to be described later are manufactured (corresponding to the sheet-like member, which is an intermediate part from which a stomach-side band member 21 and a back-side band member 25 are constructed, more specifically, a part in which the stomach-side band member 21 and the back-side band member 25 are connected in the longitudinal direction of the disposable diaper 1). Before describing the manufacturing method, the structure of the disposable diaper 1 will be described.

<<<Structure of Disposable Diaper 1>>>

Figure 1B:
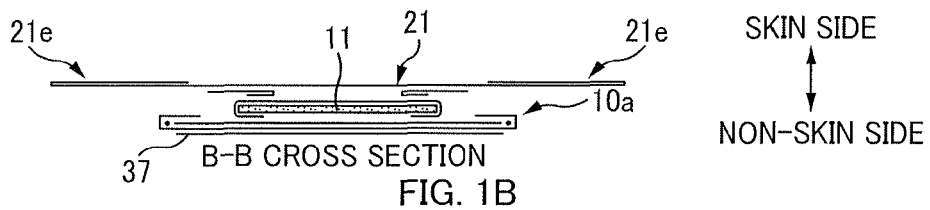
FIGS. 1B to 1D are cross-sectional views respectively taken along line B-B, line C-C, and line D-D of FIG. 1A.
Figure 1C:
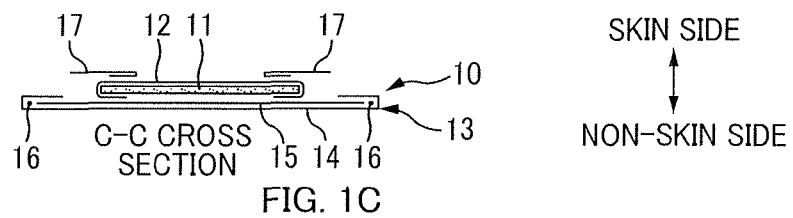
Figure 1D:
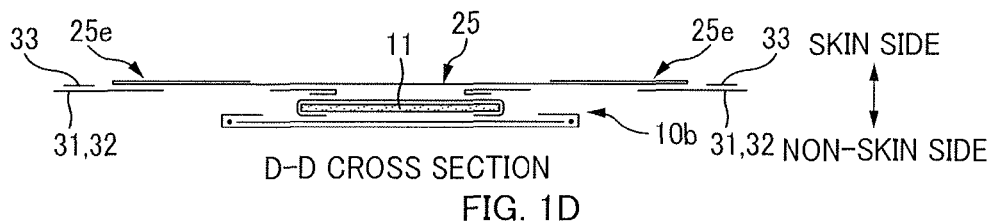
Figure 2:
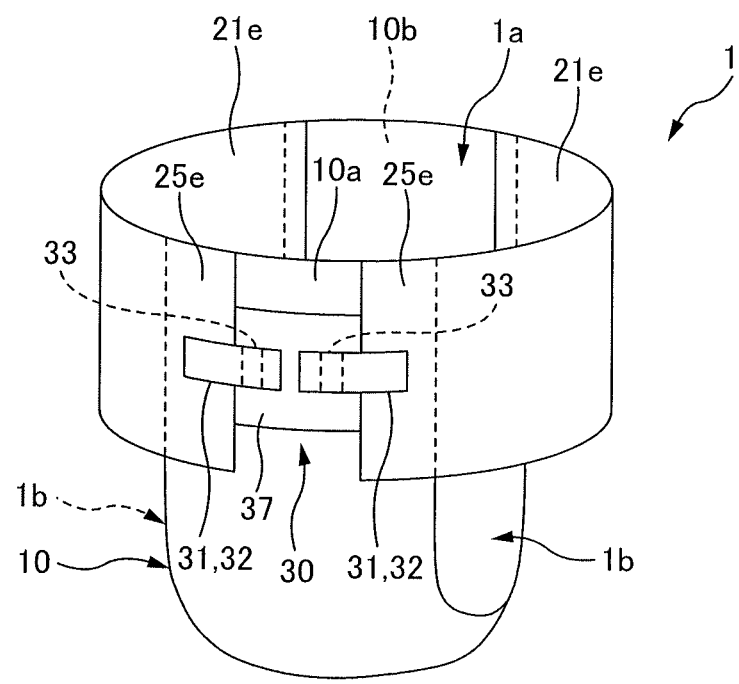
FIG. 2 is a perspective view of the disposable diaper 1 when being worn by a wearer.

FIGS. 1A to 1D and 2 are explanatory diagrams of the disposable diaper 1. FIG. 1A is a plan view of the diaper 1 in its opened condition, and FIGS. 1B to 1D are cross-sectional views respectively taken along line B-B, line C-C, and line D-D of FIG. 1A. Further, FIG. 2 is a perspective view of the diaper 1 when being worn by a wearer.

As shown in FIG. 1A, the diaper 1 includes: an absorbent main body 10 which is brought into contact with the crotch of a wearer and absorbs liquid such as exudates etc; the stomach-side band member 21 which is joined to the longitudinal front end section 10a of the absorbent main body 10 to cover the stomach side of the wearer; and the back-side band member 25 which is joined to the longitudinal rear end section 10b of the absorbent main body 10 to cover the back side of the wearer. The diaper 1 in its opened condition has a substantially H-shaped appearance when seen from above. The longitudinal direction of the diaper 1 in its opened condition coincides with the longitudinal direction of the absorbent main body 10, and the width direction (a direction perpendicular to the longitudinal direction) of the diaper 1 coincides with the width direction of the absorbent main body 10. The following descriptions assume that coincidence. It should be noted that the width direction is also referred to as the left-to-right direction.

The diaper 1 in its opened condition is doubled over at the folding position which is the longitudinal center C10 of the absorbent main body 10. Further, in this doubled over state, both end sections 25e and 25e of the back-side band member 25 in the width direction are fastened by a suitable fastening member 30 to the front end section 10a of the absorbent main body 10. As a result, a torso opening 1a and a pair of leg openings 1b and 1b shown in FIG. 2 are formed to be the diaper 1 when being worn by a wearer.

It should be noted that in the present embodiment, a detachable fastening member such as a hook-and-loop fastener, etc is used as the foregoing fastening member 30. Therefore, the diaper 1 is configured to be a so-called wrap-style (fastening type) diaper. The fastening member 30 and components 10, 21, and 25 of the diaper 1 will be described below.

As shown in FIGS. 1A to 1D, the absorbent main body 10 includes: an absorbent body 11 made of liquid absorbent fiber such as pulp fiber; a liquid-permeable surface sheet 12 which covers the absorbent body 11 from the side closer to the skin of a wearer; and a liquid-impermeable back face sheet 13 which covers the absorbent body 11 from the non-skin side (the opposite side to the surface sheet 12) and can have a two-layer structure. The surface sheet 12 can be nonwoven fabric. In this example, the surface sheet 12 wraps around the edges of the absorbent body 11 in the width direction from the skin side to the non-skin side; thereby, the surface sheet 12 covers the edges and is joined to and incorporated in the absorbent body 11 by adhesion, etc. On the other hand, the back face sheet 13 includes: an exterior sheet 14 which functions as an exterior; and a leakage-proof sheet 15 which is attached to the skin-side surface of the exterior sheet 14 and can be a liquid-impermeable film etc, as shown in FIG. 1C. The absorbent body 11 in which the surface sheet 12 is incorporated is joined by adhesion or other means to the leakage-proof sheet 15 of the back face sheet 13, thereby forming the absorbent main body 10.

It should be noted that the absorbent body 11 may contain superabsorbent polymer. Between the surface sheet 12 and the absorbent body 11, a liquid-permeable sheet such as tissue paper etc may be included.

Further, in the example of FIG. 1C, in order to form leg gathers on the end sections of the back face sheet 13 in the width direction, a stretched elastic member 16, such as rubber thread etc, is fixed to each of the end sections of the exterior sheet 14 in the width direction, along the longitudinal direction. And, these end sections are each folded inwardly in the width direction covering the elastic member 16 and the end sections of the leakage-proof sheet 15. However, this invention is not limited thereto.

Further, in the example of FIG. 1C, in order to form a pair of standing-gather sections on both end sections of the absorbent main body 10 in the width direction, standing-gather-forming sheets 17 and 17 are joined respectively to the end sections of the surface sheet 12 in the width direction. However, these sheets 17 and 17 may be omitted.

The stomach-side band member 21 is a band-shaped sheet such as nonwoven fabric etc elongated in the width direction of the diaper 1; the member 21 is made mainly of a thermoplastic resin fiber such as a polypropylene fiber (hereinafter referred to as a PP fiber) etc. The stomach-side band member 21 is, as shown in FIGS. 1A and 1B, placed extending in the width direction of the absorbent main body 10 on the longitudinal front end sections 10a. And, the stomach-side band member 21 is joined to the skin-side surface of the front end section 10a with hot-melt adhesive etc. Both end sections 21e and 21e of the stomach-side band member 21 project outwardly in the width direction from the ends of the absorbent main body 10 in the width direction. Therefore, on both the right and the left sides in the width direction of the diaper 1, a pair of first side flaps 21e and 21e are formed. Before the diaper 1 is used, the pair of first side flaps 21e and 21e are both folded up inwardly in the width direction of the diaper 1; in other words, the side flaps do not project from the ends of the absorbent main body 10 (see FIGS. 3A and 3B). Therefore, when the diaper 1 is used, as shown in FIGS. 1A and 1B, these first side flaps 21e and 21e get projected outwardly in the width direction of the diaper 1 from both ends.

In this example, these first side flaps 21e and 21e have a two-layer structure in order to reduce the wearer's skin stress. More specifically, as shown in FIG. 1B, the end sections of the stomach-side band member 21, which are the first side flaps 21e and 21e, are each folded inwardly in the width direction of the diaper 1. In addition, the facing surfaces overlay each other and are fixed in close contact by crimping or other means. Therefore, the first side flaps 21e and 21e have a two-layer structure.

The back-side band member 25 is also a band-shaped sheet such as nonwoven fabric etc elongated in the width direction of the diaper 1; the member 25 is made mainly of a thermoplastic resin fiber such as a PP fiber etc. The back-side band member 25 is, as shown in FIGS. 1A and 10, placed extending in the width direction of the absorbent main body 10 on the longitudinal rear end section 10b, and is joined to the skin-side surface of the rear end section 10b with hot-melt adhesive etc. Both end sections 25e and 25e of the back-side band member 25 also project outwardly in the width direction from the ends of the absorbent main body 10 in the width direction. Therefore, on both the right and the left sides in the width direction of the diaper 1, a pair of second side flaps 25e and 25e are formed. Further, similarly to the foregoing first side flap 21e, before the diaper 1 is used, the pair of second side flaps 25e and 25e are both folded up inwardly in the width direction of the diaper 1; in other words, the side flaps do not project from the ends the absorbent main body 10 (see FIGS. 3A and 3C). Therefore, when the diaper 1 is used, as shown in FIGS. 1A and 1D, these second side flaps 25e and 25e are opened and get projected outwardly in the width direction of the diaper 1 from both ends.

Further, similarly to the foregoing first side flap 21e, these second side flaps 25e and 25e also have a two-layer structure in order to reduce the wearer's skin stress. More specifically, as shown in FIG. 1D, the end sections of the back-side band member 25, which are the second side flaps 25e and 25e, are each folded inwardly in the width direction of the diaper 1. In addition, the facing surfaces overlay each other and are fixed in close contact by crimping or other means. Therefore, the second side flaps 25e and 25e also have a two-layer structure.

Fastening member 30, as shown in FIGS. 1A, 1B, 1D, and 2, includes: fastening tapes 31 and 31 which are disposed respectively at the end sections of the pair of second side flaps 25e and 25e; and a target tape 37 which is made of nonwoven fabric and disposed of the surface on the non-skin side of the front end section 10a of the absorbent main body 10 so as to removably engage with these fastening tapes 31 and 31.

As shown in FIGS. 1A and 1D, each fastening tape 31 has a tape substrate 32, which is a rectangular band-shaped sheet. One longitudinal end section of the tape substrate 32 is fixed to the end section of the second side flap 25e, and the other end section extends outwardly in the width direction beyond the end section of the second side flap 25e. To the extending section, a male component 33 of a hook-and-loop fastener is fixed. In the fastened state shown in FIG. 2, the male component 33 engages with the target tape 37.

Figure 3A:
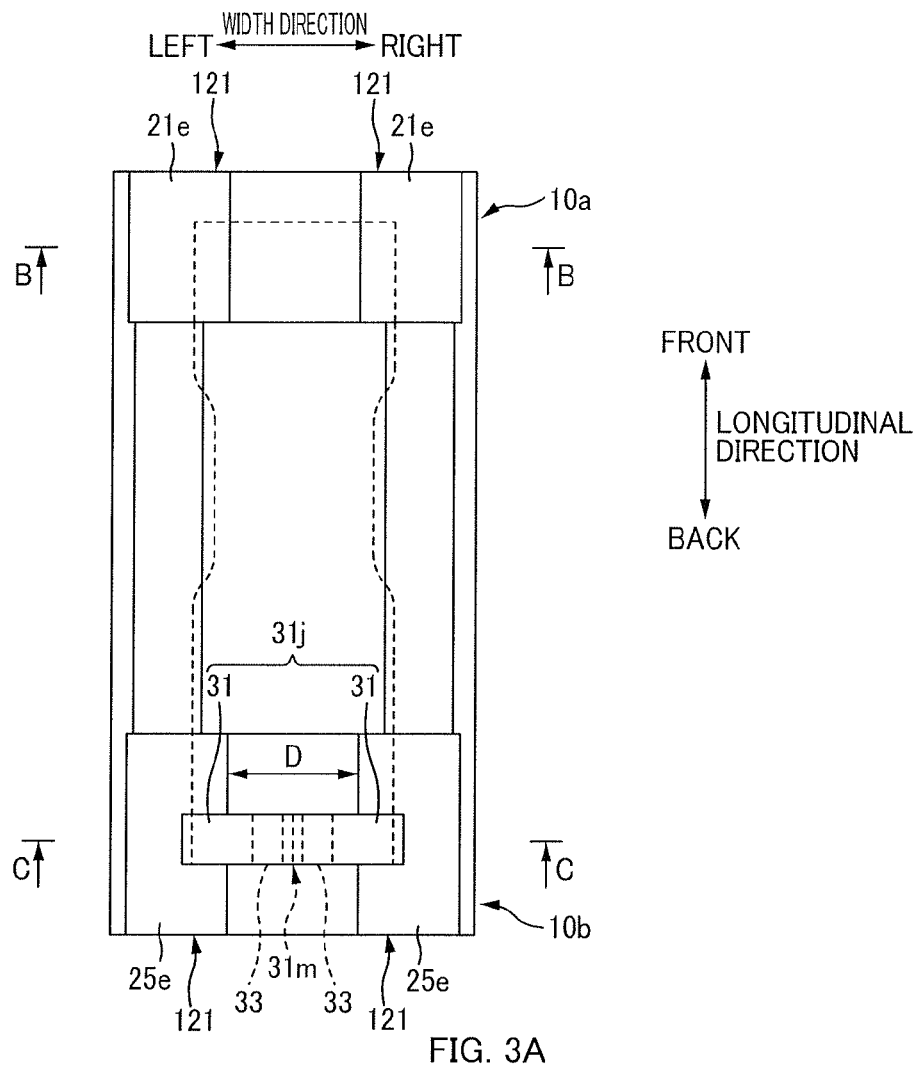
FIG. 3A is a plan view of the disposable diaper 1 when the first and second side flaps 21e and 25e are folded up.
Figure 3B:
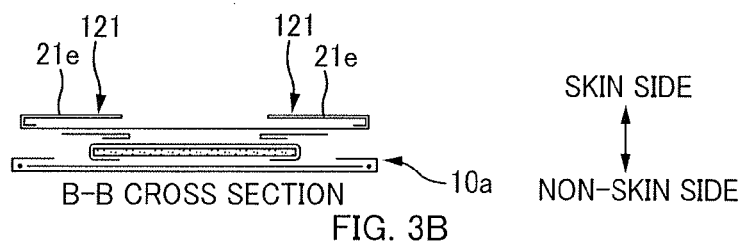
FIGS. 3B and 3C are cross-sectional views respectively taken along line B-B and line C-C of FIG. 3A.
Figure 3C:
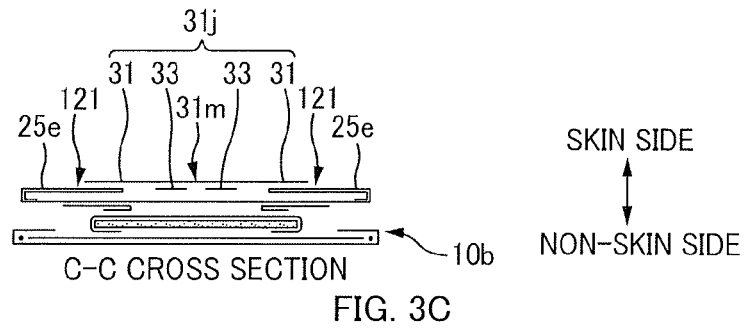

FIGS. 3A to 3C are explanatory diagrams of the fastening tape 31 before use. FIG. 3A is a plan view of the diaper 1 before use, and FIGS. 3B and 3C are cross-sectional views respectively taken along line B-B and line C-C of FIG. 3A.

As mentioned above, before the diaper 1 is used, the second side flaps 25e and 25e are each folded up inwardly in the width direction of the diaper 1 (See FIGS. 3A to 3C). Therefore, the end sections of the pair of second side flaps 25e and 25e each face inwardly in the width direction of the diaper 1 and are lined up with the space D between them on both the right and the left sides in the width direction. On the other hand, at this stage, a pair of fastening tapes 31 and 31 are still connected by perforations 31m to each other, to form a member 31j. This connected body 31j of the fastening tape 31 extends over and is joined to the end sections of the pair of second side flaps 25e and 25e.

When the diaper 1 is used, firstly, the connected body 31j is separated by the perforations 31m into the pair of fastening tapes 31 and 31. Thereafter, each fastening tape 31 is opened outwardly in the width direction together with the second side flap 25e. Therefore, each fastening tape 31 becomes in a state where it can be fastened, and projects outwardly in the width direction of the diaper 1, as shown in FIGS. 1A and 1D.

<<<Manufacturing Method for Band-Member Intermediate Part 20 Associated with Disposable Diaper 1>>>

(1) Manufacturing Method for Diaper 1

Figure 4:
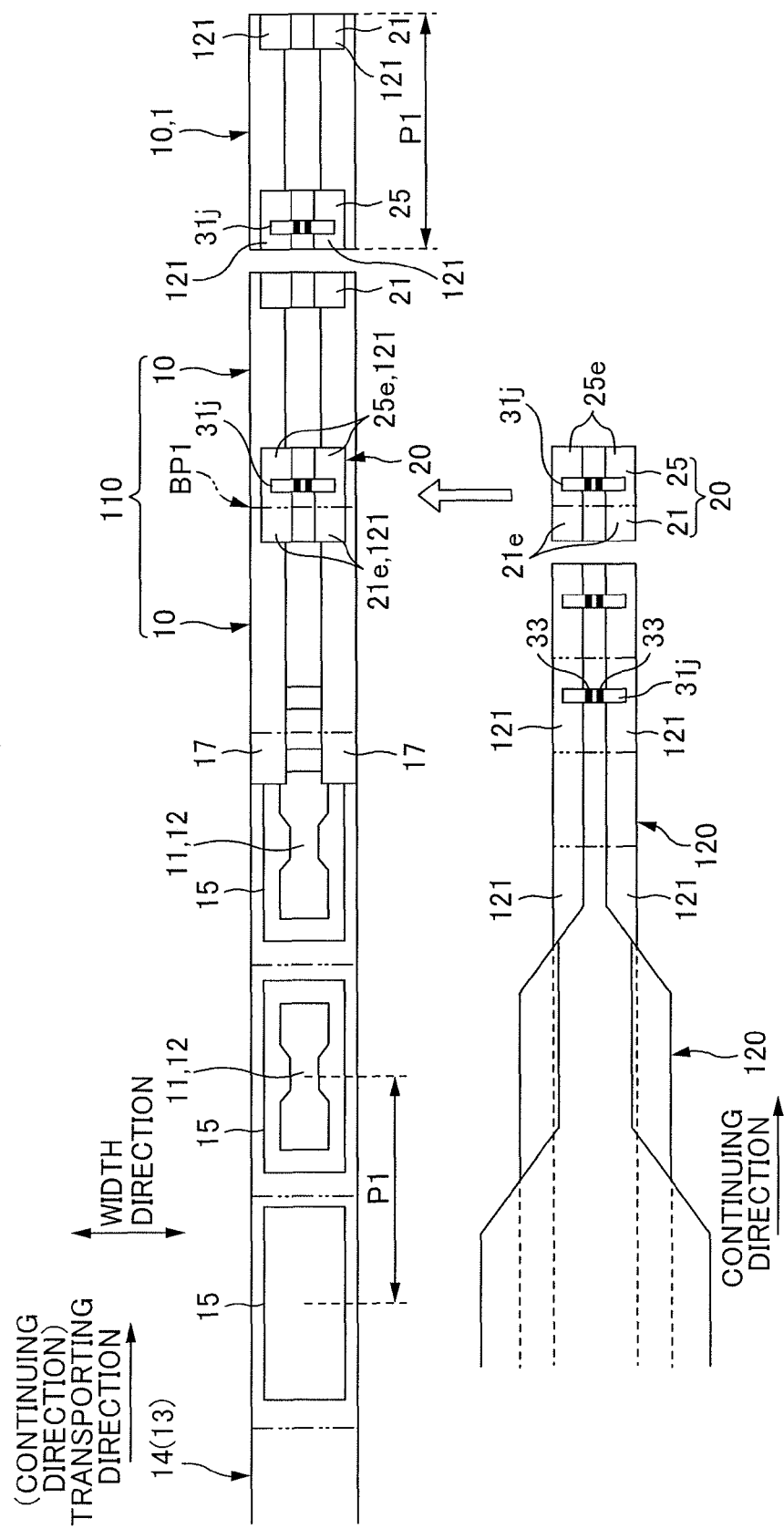
FIG. 4 is an explanatory diagram of a manufacturing method for the diaper 1.

Before the description of the manufacturing method for the band-member intermediate part 20 according to the present embodiment, the manufacturing method for the disposable diaper 1 will be described briefly. FIG. 4 is an explanatory diagram of the manufacturing method for the diaper 1, being a plan view showing how the diaper 1 is processed to be a finished product.

In the manufacturing method for the diaper 1, there are two parts-production lines, for example. In the first parts-production line, a continuous body 110 of the absorbent main body 10 is produced, as shown in the upper diagram of FIG. 4. The continuous body 110 of the absorbent main body 10 consists of a plurality of the absorbent main bodies 10 that are continuous in the longitudinal direction thereof. In this example, a plurality of the absorbent main bodies 10, 10 . . . lined up in the transporting direction are connected in the transporting direction by the exterior sheet 14 related to the back face sheet 13. That is, the exterior sheet 14 at this stage is the continuous sheet 14 that is continuous in the transporting direction. While this continuous sheet 14 is being conveyed in the transporting direction by a suitable transporting apparatus (corresponding to the fifth unit) such as a suction conveyor etc, the leakage-proof sheet 15, the absorbent body 11 and the like are intermittently processed in a sequence on the continuous sheet 14 with a product pitch P1 by joining or other means. And, the continuous body 110 of the absorbent main body 10 is produced.

On the other hand, in the second parts-production line, the band-member intermediate part 20 is produced, as shown in the lower diagram of FIG. 4. The band-member intermediate part 20 consists of the stomach-side band member 21 and the back-side band member 25 which are connected in the longitudinal direction of the diaper 1. At this stage, both end sections in the width direction, which will be first side flaps 21e and 21e and second side flaps 25e and 25e, are still folded up inwardly in the width direction. In addition, the connected body 31j of the fastening tape 31 extends over and is joined to both end sections which are folded up inwardly.

The band-member intermediate part 20 which is produced in the aforementioned form is finally supplied to the foregoing first parts-production line. In this line, as shown in the upper diagram of FIG. 4, the band-member intermediate part 20 is placed on and joined to the continuous body 110 of the absorbent main body. At this stage, the intermediate part 20 on the continuous body 110 of the absorbent main body is adjusted to a position so as to extend over the position BP1 which is the boundary between the adjacent absorbent main bodies 10 and 10 in the transporting direction. Then, by dividing the continuous body 110 of the absorbent main body at the boundary position BP1, the band-member intermediate part 20 is divided into the stomach-side band member 21 and the back-side band member 25. Therefore, the diaper 1 is finished.

After joining of the band-member intermediate part 20 to the continuous body 110 of the absorbent main body which is described immediately above, the continuous body 110 continues to be conveyed for a while. Further, at this stage, as mentioned above, the first and second side flaps 21e and 25e of the band-member intermediate part 20 are each folded up inwardly in the width direction. However, it is possible that air resistance, etc in the conveying opens up the first and second side flaps 21e and 25e, resulting in some problems such as being entrapped by devices around the conveying path.

Therefore, in the manufacturing method for the band-member intermediate part 20 used in the second parts-production line, the first and second side flaps 21e and 25e are temporarily secured in a folded-up state by embossing these flaps; this will be described later. However, in some cases, it may not be sufficient. Therefore, in addition thereto, the configuration is designed in order to maintain the flaps in a folded-up state.

Below, this technique and the manufacturing method for the band-member intermediate part 20 will be described in detail.

(2) Manufacturing Method for Band-Member Intermediate Part 20

Figure 5:
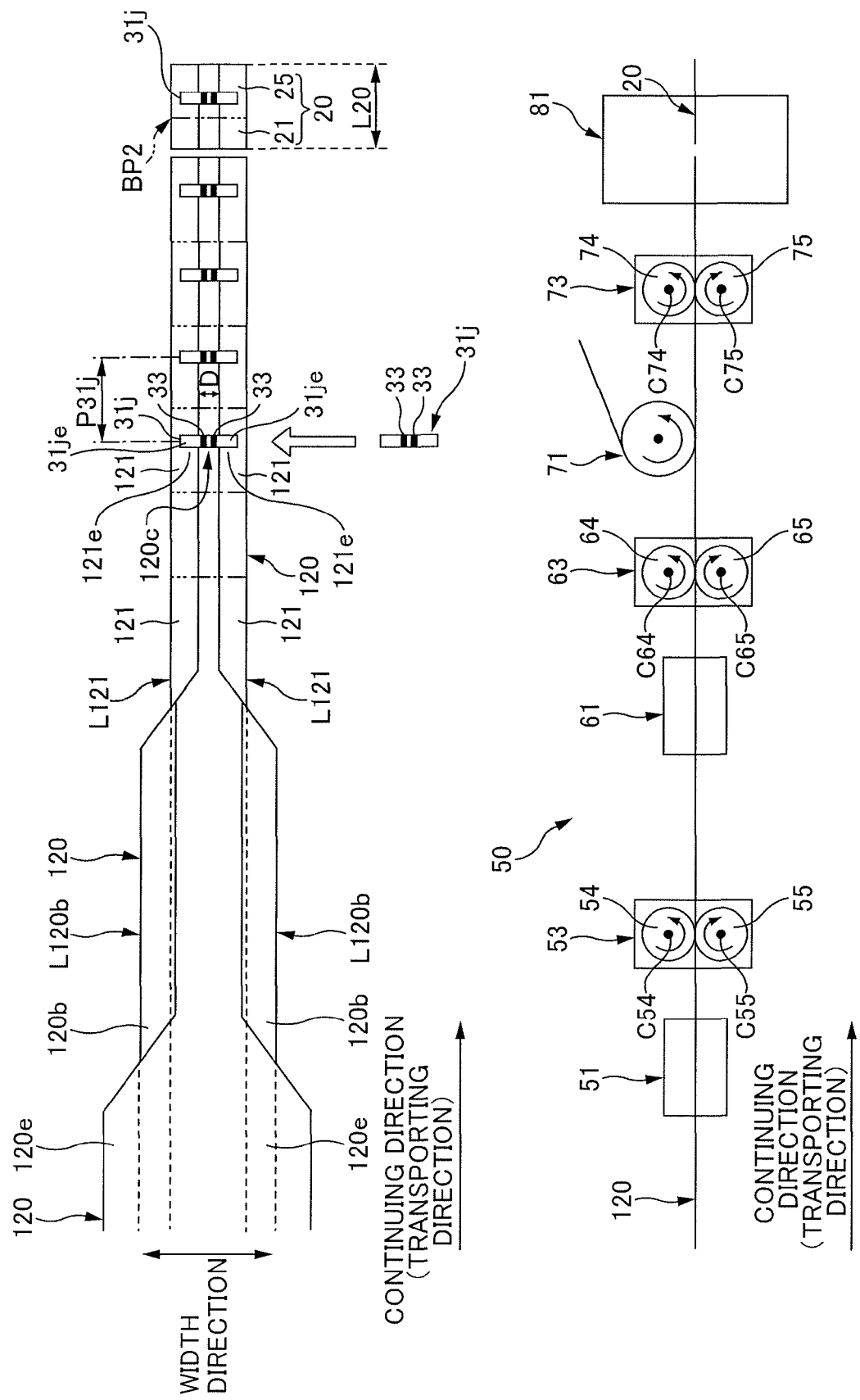
FIG. 5 is an explanatory diagram of a manufacturing method for a band-member intermediate part 20 according to the present embodiment.

FIG. 5 is an explanatory diagram of the manufacturing method for the band-member intermediate part 20. The upper diagram of FIG. 5 is a plan view showing the production process of the band-member intermediate part 20, and the lower diagram of FIG. 5 is a side view of the outline of a manufacturing apparatus 50 corresponding to the production process.

Firstly, the continuous sheet 120 of nonwoven fabric, which is the web of the band-member intermediate part 20, is continuously drawn from a reel or other devices. While conveying the supplied continuous sheet 120 along its continuing direction, the continuous sheet 120 passes through a first continuous-folding-plate device 51 on its conveying path. Therefore, while passing through the first continuous-folding-plate device 51, the end sections 120e and 120e of the continuous sheet 120 in the width direction are each folded inwardly in the width direction, and a pair of folded sections 120b and 120b are formed. It should be noted that these folded sections 120b and 120b become the aforementioned first side flaps 21e and 21e and second side flaps 25e and 25e, which have a two-layer structure (See FIGS. 1B and 1D). Further, the first continuous-folding-plate device 51 may include a guide plate (not shown) which, in order to fold up the end sections 120e and 120e, gradually guides the end sections 120e and 120e inwardly in the width direction with the conveyance of the continuous sheet 120.

Thereafter, in order to fix these folded sections 120b and 120b in a folded state, the continuous sheet 120 passes through a first embossing unit 53 on its conveying path. Thereby; the surfaces of the folded section 120b which are to overlay each other are crimped and joined.

More specifically, as shown in the lower diagram of FIG. 5, the first embossing unit 53 includes a pair of upper and lower rolls 54 and 55. The pair of rolls 54 and 55 are driven and rotate about predetermined respective rotational axes C54 and C55 with the outer circumferential surfaces thereof facing each other. With this configuration, the rotating direction becomes the transporting direction, which is the continuing direction of the continuous sheet 120. The upper roll 54 is a so-called embossing roll. That is, on its outer circumferential surface, a plurality of embossing protrusions (not shown) are arranged along the entire length in the circumferential direction of the embossing roll, in a predetermined arrangement pattern such as a staggered pattern, etc. On the other hand, the lower roll 55 is a so-called anvil roll. That is, its outer circumferential surface is smooth so as to receive the embossing protrusions. Therefore, when the continuous sheet 120 passes through the nip between these rolls 54 and 55, the folded sections 120b and 120b are each pressed by the embossing protrusions of the embossing roll 54 and the outer circumferential surface of the anvil roll 55, to be fixed in a folded state.

It is desirable that the first embossing unit 53 includes a heating device such as a heater and that at least either one of the embossing roll 54 and the anvil roll 55 is heated by the heating device. In this case, the continuous sheet 120 is properly plasticized, to increase the strength of joining (crimping) associated with the fixing of the folded section 120b. It should be noted that, if the material of the continuous sheet 120 has a softening point, the roll is preferably heated while adjusting the temperature of the outer circumferential surface thereof to be lower than the softening point. For example, if the continuous sheet 120 is made of PP fiber, the softening point of PP fiber is 130° C. Therefore, the temperature of the outer circumferential surface is adjusted to be 100° C.±10° C. This can prevent the continuous sheet 120 from being damaged.

Further, it is desirable that, at a reasonable time before the folding, hot-melt adhesive, etc is previously applied to at least either one of the surfaces of the folded section 120b which are to overlay each other. In this case, the surfaces are joined with adhesive so that the folded section 120b is fixed more firmly in a folded state.

Next, the continuous sheet 120 on which the folded section 120b is formed passes through a second continuous-folding-plate device 61 (corresponding to the first unit) on its conveying path. Therefore, while passing through the second continuous-folding-plate device 61, the folded sections 120b and 120b of the continuous sheet 120 are each folded up more inwardly in the width direction, and a pair of folded-up sections 121 and 121 are formed. It should be noted that, unlike the foregoing folded section 120b, the folded-up sections 121 are opened up when the diaper 1 is used. In other words, when using the diaper 1, the folded-up sections 121 are released from their folded-up state, are opened up, and function as the first side flap 21e or the second side flap 25e. Hereinafter, the folded-up section 121 is also referred to as a sideflap-folded-up section 121.

Figure 6:
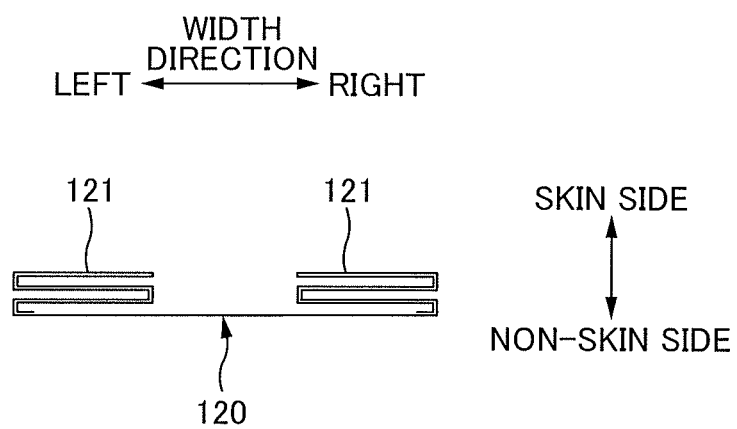
FIG. 6 is an explanatory diagram showing how to fold up a sideflap-folded-up section 121 in the modified example.

The section may be folded one time so that it has a V-shaped cross section, as shown in FIG. 5 (that is, the example shown in FIGS. 3B and 3C). Also, the section may be folded three times so that it has an M-shaped cross section, as shown in the cross-sectional view of FIG. 6, which is an example of multiple (an odd number of) foldings.

Further, the second continuous-folding-plate device 61 may include a guide plate (not shown) which, in order to fold up the folded section 120b, gradually guides the folded section 120b inwardly in the width direction with the conveyance of the continuous sheet 120.

Thereafter, in order to temporarily secure these side-flap folded-up sections 121 and 121 in a folded-up state, the continuous sheet 120 passes through a second embossing unit 63 (corresponding to the second unit and the third unit) on its conveying path. Thereby the surfaces of the sideflap-folded-up section 121 which are to overlay each other are crimped and temporarily joined.

The term "temporarily joining" herein means joining the surfaces so that they can be separated and used; in other words, joining in such a manner that the surfaces of the sideflap-folded-up section 121 can be easily separated at a later time of use without impairing the function of the side flaps 21e and 25e. The strength of the joining can be, for example, 0.1-0.4 N/25 mm, preferably 0.2 N/25 mm.

The second embossing unit 63 which performs the foregoing temporary-securing has a similar configuration to the foregoing first embossing unit 53, as shown in the lower diagram of FIG. 5. That is, this apparatus includes a pair of upper and lower rolls 64 and 65. The pair of rolls 64 and 65 are driven and rotate about predetermined respective rotational axes C64 and C65 with the outer circumferential surfaces thereof facing each other. With this configuration, the rotating direction becomes the transporting direction, which is the continuing direction of the continuous sheet 120. The upper roll 64 is an embossing roll (corresponding to the pressing member). That is, on its outer circumferential surface, a plurality of embossing protrusions 66 (See FIG. 7) are arranged along the entire length in the circumferential direction of the embossing roll, in a predetermined arrangement pattern such as a grid pattern, etc. On the other hand, the lower roll 65 is an anvil roll. That is, its outer circumferential surface is smooth so as to receive the embossing protrusions 66. Therefore, when the continuous sheet 120 passes through the nip between these rolls 64 and 65, the folded-up sections 121 and 121 are each pressed by the embossing protrusions 66 of the embossing roll 64 and the outer circumferential surface of the anvil roll 65, to be temporarily secured in a folded-up state.

Figure 7:
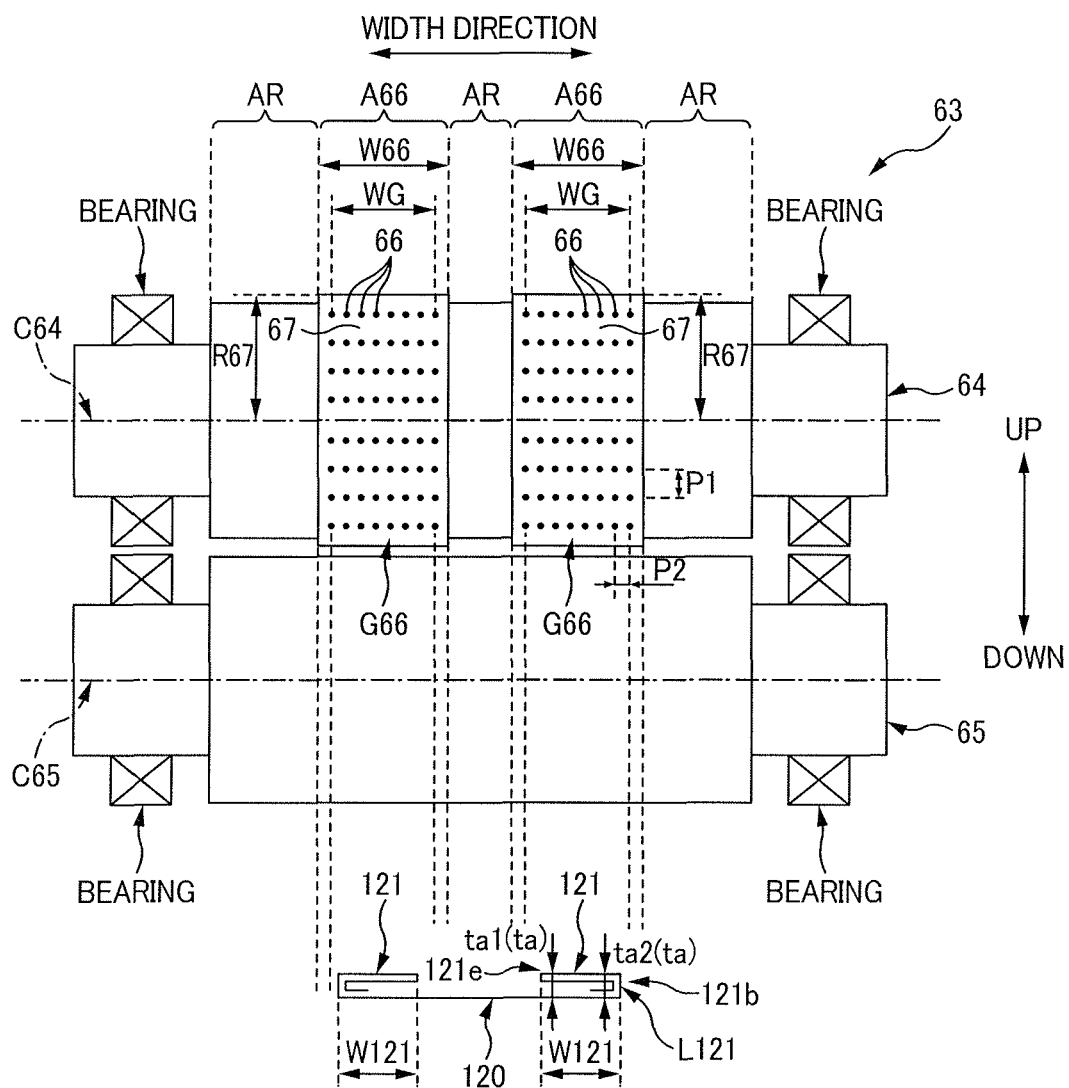
FIG. 7 is a front view of an embossing roll 64 and an anvil roll 65 associated with the second embossing unit 63.

FIG. 7 is a front view of these embossing roll 64 and anvil roll 65. It should be noted that, below the front view, a longitudinal sectional view of the continuous sheet 120 passing through the nip between these rolls 64 and 65 is illustrated.

In this illustrated example, two areas in the direction along the rotational axis C64 of the embossing roll 64 are set as the areas A66 in which the embossing protrusions 66 are disposed on the outer circumferential surface of the embossing roll 64 (hereinafter also referred to as a protrusion area A66). The protrusion areas A66 correspond to the pair of side-flap folded-up sections 121 and 121, and have a predetermined width W66 in that direction. In each of protrusion areas A66, a plurality of embossing protrusions 66 are placed in a grid arrangement to form a group. Hereinafter this group is referred to as an embossing protrusion group G66. It should be noted that the width WG in the direction along the rotational axis C64 of the embossing protrusion group G66 is slightly narrower than the width W66 of the protrusion area A66.

Further, concerning a portion 67 in each protrusion area A66 which is not the embossing protrusion 66, that is the portion 67 surrounding the embossing protrusion 66 in each protrusion area A66, the roll diameter R67 thereof is set to be larger than that of a remaining area AR which is on the outer circumferential surface of the embossing roll 64 but is an area that is not the protrusion area A66. With this configuration, the nip between the anvil roll 65 and the portion 67 in the protrusion area A66 which is not the embossing protrusion 66 is narrower than the nip between the anvil roll 65 and the remaining area AR.

This is for effectively creasing the side-flap folded-up sections 121.

More specifically, in the protrusion area A66 (corresponding to the pressing region), not only the embossing protrusion 66 but also the portion 67 surrounding the embossing protrusion 66 (the portion 67 which is not the embossing protrusion 66) press (pinch) the sideflap-folded-up section 121 co-operating with the smooth outer circumferential surface of the anvil roll 65. With this configuration, either one of the embossing protrusion 66 and the portion 67 surrounding the embossing protrusion 66 constantly comes into contact with and presses the sideflap-folded-up section 121 along the entire length thereof in the direction of the fold line L121 of the sideflap-folded-up section 121. In other words, the sideflap-folded-up section 121 is continuously pressed along the direction of the fold line L121. Therefore, the sideflap-folded-up section 121 is reliably creased along the entire length thereof in that direction while the surfaces which overlay each other are in close contact. In other words, the gap between the surfaces becomes flat and suppressed along the entire length thereof in that direction. Further, by the pressing, the thickness of the sideflap-folded-up section 121 becomes smaller along the entire length thereof in that direction. Therefore, it is far less likely to encounter air resistance in conveying. This can effectively prevent such a problem of the air resistance in conveying causing the temporarily-secured surfaces of the sideflap-folded-up section 121 to separate and the section 121 to open, as mentioned above.

It should be noted that in order to definitely achieve the foregoing "pressing the portion 67 surrounding the embossing protrusion 66 in the protrusion area A66," the following conditions are required to be satisfied. Firstly, the nip size (distance) between the portion 67 surrounding the embossing protrusion 66 in the protrusion area A66 and the outer circumferential surface of the anvil roll 65 has to be smaller than the thickness ta of the sideflap-folded-up section 121 but not zero; the thickness ta is the thickness of the materials which are to pass through the nip between the embossing roll 64 and the anvil roll 65. In addition thereto, because there are the embossing protrusions 66 in the protrusion area A66, the projecting height of the embossing protrusion 66 relative to the surrounding portion 67 is required to be smaller than the nip size, as a matter of course.

The foregoing "the thickness ta of the sideflap-folded-up section 121" means the total thickness ta of all materials which overlay one another in a folded up state (see the lower section of FIG. 7, for example). It should be noted that the total thickness ta can be measured as the distance between a pair of measuring plungers included in a thickness gauge (PEACOK DIAL THICKNESS GAUGE No. I1352) when the entire area of a squared sample having dimensions of 10 cm×10 cm is pinched by the pair of measuring plungers at a pressure of 3 (g/cm2) in the thickness direction.

However, if the total thickness ta of all materials is different depending on the position in the width direction, the total thickness of a thick portion associated with the sideflap-folded-up section 121 can be the foregoing "total thickness ta." However, it is more desirable that the total thickness of a thin portion is the "total thickness ta."

For example, in the example of FIG. 7, the end section 121e of the sideflap-folded-up section 121 has a three-layer structure consisting of three layers of material. The root section 121b of the same section 121, at the position of the fold line L121, has a four-layer structure consisting of four layers of material. That is, the total thicknesses ta1 and ta2 are different from each other. In this case, the total thickness ta2 of the root section 121b may be the "total thickness ta." However, it is more desirable that the total thickness ta1 of the end section 121e, which is smaller than the root section 121b, is the "total thickness ta." In this case, the sideflap-folded-up section 121 can be reliably pressed along the entire width W121 thereof. This enables the side-flap folded-up sections 121 to be more reliably maintained in a folded-up state. On the other hand, even if the total thickness ta2 of the root section 121b is "total thickness ta," the peripheral portion of the fold line L121 can be continuously pressed along the direction of the fold line L121. This can decrease a large force for recovery from the folding which may be produced in the peripheral portion of the fold line L121. Therefore, this is effective to maintain the folded-up state.

Further, the arrangement pattern of the embossing protrusions 66 is not limited to a grid pattern in the example of FIG. 7. A staggered pattern may be employed, and any other patterns may also be employed. Further, the arrangement pitch P1 in the circumferential direction associated with the arrangement pattern of the protrusions 66 and the arrangement pitch P2 in the direction along the rotational axis C64 can be selected from 5-10 mm. However, the invention is not limited thereto. Further, concerning the shape of the embossing protrusion 66, for example, the front end side thereof can be smaller in size than the root side; that is, the longitudinal cross-section of the protrusion 66 can be substantially trapezoidal, etc in shape. However, the invention is not limited thereto. Further, the planar shape of the top surface of the embossing protrusion 66 can be for example a circle or a polygon, and the area of the top surface can be for example 0.19-3.14 mm². However, the invention is not limited thereto.

By the way, if hot-melt adhesive is used for fixing the folded section 120b as mentioned above, it is desirable that before the hot-melt adhesive loses its fluidity the continuous sheet 120 passes through the second embossing unit 63. In this case, by pressing the abovementioned embossing roll 64 and anvil roll 65 which are for the foregoing temporary-securing and creasing, the hot-melt adhesive on the folded section 120b can move in the thickness direction and soak through and in between the surfaces of the sideflap-folded-up section 121 which overlay each other. As a result, the adhesive not only assists in the aforementioned temporarily-securing, but also removes the wrinkles of the sideflap-folded-up section 121 as happens with sized fabric, resulting in additional suppression of the gap between the surfaces.

Further, it is desirable that, similarly to the abovementioned first embossing unit 53, the second embossing unit 63 also includes a heating device such as a heater, and that at least one of the embossing roll 64 and the anvil roll 65 is heated by the heating device. In this case, the continuous sheet 120 is properly plasticized, and this enables the sideflap-folded-up section 121 to be more firmly creased. It should be noted that, if the material of the continuous sheet 120 has a softening point, the roll is preferably heated while adjusting the temperature of the outer circumferential surface thereof to be lower than the softening point. For example, if the continuous sheet 120 is made of PP fiber, the softening point of PP fiber is 130° C. The temperature of the outer circumferential surface is adjusted to be 100° C.±10° C. This can prevent the continuous sheet 120 from being damaged.

Further, as shown in FIG. 7, it is desirable that the width WG of each embossing protrusion group G66 and the width W66 of each protrusion area A66 is larger than the width W121 of the sideflap-folded-up section 121. With such a configuration, even if the continuous sheet 120 which is being conveyed is somewhat meandering in the width direction, the sideflap-folded-up section 121 can be temporarily secured and creased reliably.

Next, as shown in FIG. 5, the continuous sheet 120 on which the side-flap folded-up sections 121 and 121 are formed passes through a first transfer device 71 on its conveying path. This first transfer device 71 supplies the connected body 31j of the fastening tape 31 with a predetermined supply pitch P31j towards the transporting direction, which is the continuing direction of the continuous sheet 120. As shown in the upper diagram of FIG. 5, the connected body 31j of the fastening tape 31 extends over the end sections 121e and 121e of the side-flap folded-up sections 121 and 121, and both end sections 31je and 31je of that connected body 31j are each joined with hot-melt adhesive etc to the end sections 121e and 121e, which face inwardly in the width direction of the continuous sheet 120.

It should be noted that at this time the end sections 121e and 121e of the side-flap folded-up sections 121 and 121 have the space D between them. Further, in the space D, a pair of the male components 33 and 33 of the hook-and-loop fastener are located, the pair of male components 33 and 33 being disposed in the central section of the connected body 31j of the fastening tape 31. Therefore, the pair of male components 33 and 33 of the hook-and-loop fastener face the central section 120c of the continuous sheet 120 over the space D. Therefore, when extending over the end sections mentioned above, the male components 33 and 33 of the hook-and-loop fastener comparatively easily engage with the central section 120c of the continuous sheet 120. As a result, in the subsequent conveyance, the connected body 31j of the fastening tape 31 assists in the maintaining of the side-flap folded-up sections 121 and 121 in a folded-up state.

Thereafter, in order to more firmly join both end sections 31je and 31je of the connected body 31j of the fastening tape 31 to the side-flap folded-up sections 121 and 121, the continuous sheet 120 passes through a third embossing unit 73 on its conveying path. Therefore, both end sections 31je and 31je of the connected body 31j of the fastening tape 31 are respectively pressed onto the side-flap folded-up sections 121 and 121.

The third embossing unit 73 which performs the pressing has a similar configuration to the foregoing first and second embossing processing apparatuses 53 and 63, as shown in the lower diagram of FIG. 5. That is, this apparatus includes a pair of upper and lower rolls 74 and 75. The pair of rolls 74 and 75 are driven and rotate about predetermined respective rotational axes C74 and C75 with the outer circumferential surfaces thereof facing each other. With this configuration, the rotating direction becomes the transporting direction, which is the continuing direction of the continuous sheet 120. The upper roll 74 is an embossing roll. That is, on its outer circumferential surface, a plurality of embossing protrusions 76 (See FIG. 8) are arranged along the entire length in the circumferential direction of the embossing roll, in a predetermined arrangement pattern such as a staggered pattern, etc. On the other hand, the lower roll 75 is an anvil roll. That is, its outer circumferential surface is smooth so as to receive the embossing protrusions 76. Therefore, when the continuous sheet 120 passes through the nip between these rolls 74 and 75, both end sections 31je and 31je of the connected body 31j of the fastening tape 31 are each pressed by the embossing protrusion 76 of the embossing roll 74 and the outer circumferential surface of the anvil roll 75 to the end sections 121e and 121e of the corresponding side-flap folded-up sections 121 and 121. As a result, adhesion of the hot-melt adhesive becomes more firm.

Figure 8:
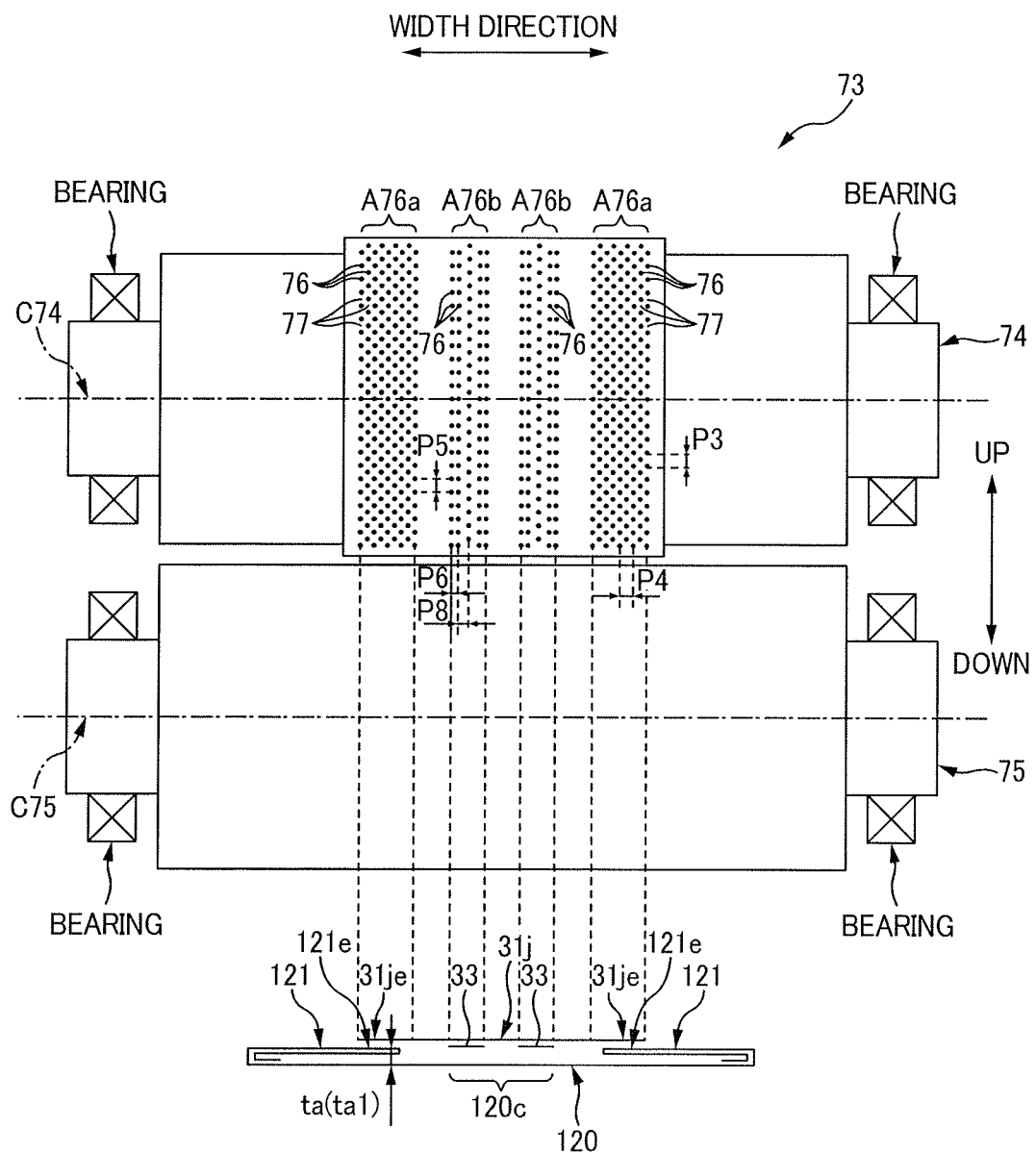
FIG. 8 is a front view of an embossing roll 74 and an anvil roll 75 associated with the third embossing unit 73.

FIG. 8 is an explanatory diagram of the protrusion areas A76a and A76b on the outer circumferential surface of the embossing roll 74 where the embossing protrusions 76 are placed; a plan view of the embossing roll 74 and the anvil roll 75. Further, in the lower section of FIG. 8, the cross-sectional view of the continuous sheet 120 to which the connected body 31j of the fastening tape 31 is joined is shown so that the embossing protrusions 76 and the corresponding target positions to be pressed on the connected body 31j of the fastening tape 31 can be seen.

Four areas in a direction along the rotational axis C74 of the embossing roll 74 are set as the protrusion areas A76a and A76b. Two outer protrusion areas A76a and A76a in the direction along the rotational axis C74 are respectively defined at the positions corresponding to both end sections 31je and 31je of the connected body 31j of the fastening tape 31. With this configuration, the protrusion areas A76a and A76a press both end sections 31je and 31je of the connected body 31j, respectively to the end sections 121e and 121e of the corresponding side-flap folded-up sections 121 and 121.

It should be noted that the illustrated arrangement pattern of the embossing protrusions 76 in the protrusion area A76a is a staggered pattern. However, the invention is not limited thereto. Further, the arrangement pitch P3 of the arrangement pattern in the circumferential direction and the arrangement pitch P4 in the direction along the rotational axis C74 can be selected from 3.0-5.0 mm. However, the invention is not limited thereto. Further, concerning the shape of the embossing protrusion 76, for example, the front end side thereof can be smaller in size than the root side; that is, the longitudinal cross-section of the protrusion 76 can be substantially trapezoidal, etc in shape. However, the invention is not limited thereto. Further, the planar shape of the top surface of the embossing protrusion 76 can be for example a circle or a polygon, and the area of the top surface can be for example 0.19-3.14 $mm^2$. However, the invention is not limited thereto.

On the other hand, two inner protrusion areas A76b and A76b are each defined at the corresponding positions to the pair of male components 33 and 33 of the hook-and-loop fastener included in the connected body 31j of the fastening tape 31. With this configuration, the protrusion areas A76b and A76b press respectively the pair of male components 33 and 33 to the central section 120c of the continuous sheet 120 in the width direction, to further increase the force of the engagement of each of the male components 33 and 33 with the continuous sheet 120. As a result, the connected body 31j assists greatly in the maintaining of the side-flap folded-up sections 121 and 121 in a folded-up state during the subsequent conveyance.

It should be noted that the illustrated arrangement pattern of the embossing protrusions 76 in the protrusion area A76b is substantially a grid pattern. However, this invention is not limited thereto. Further, the arrangement pitch P5 of the arrangement pattern in the circumferential direction and the spacing P6 and P8 in the direction along the rotational axis C74 can be selected from 2.5-4.0 mm. However, this invention is not limited thereto.

It is desirable that the nip size (distance) between the embossing protrusion 76 of the protrusion area A76a and the outer circumferential surface of the anvil roll 75 is smaller than the thickness ta of the sideflap-folded-up section 121 at the position of the end section 121e but not zero. With such a configuration, the embossing protrusions 76 in the protrusion area A76a, co-operating with the anvil roll 75, can effectively press (pinch) the portions of the end section 121e of the sideflap-folded-up section 121 to which the connected body 31j of the fastening tape 31 is not joined. As a result, the sideflap-folded-up section 121 can be more firmly creased.

It is more desirable that the nip size (distance) between a portion 77 surrounding the embossing protrusion 76 in the protrusion area A76a and the outer circumferential surface of the anvil roll 75 is smaller than the thickness ta of the sideflap-folded-up section 121 at the position of the end section 121e. With such a configuration, in addition to the pressing by the foregoing embossing protrusions 76, the portion 77 surrounding the embossing protrusion 76 can effectively press the portions of the sideflap-folded-up section 121 to which the connected body 31j is not joined. As a result, the sideflap-folded-up section 121 can be far more firmly creased.

Then, as the final step, the continuous sheet 120 to which the connected body 31j of the fastening tape 31 is joined passes through a second transfer device 81 (corresponding to the fourth unit) on its conveying path, as shown in FIG. 5. In the second transfer device 81, as shown in the upper diagram of FIG. 5, the continuous sheet 120 is divided with a predetermined pitch L20 to produce the band-member intermediate part 20, and the band-member intermediate part 20 is supplied to the abovementioned first parts-production line. As shown in the upper diagram of FIG. 4, the band-member intermediate part 20 is joined to the continuous body 110 of the absorbent main body 10 which is being conveyed in the line.

It should be noted that, thereafter the band-member intermediate part 20 is conveyed and substantially incorporated in the continuous body 110 of the absorbent main body 10. At this time, the sideflap-folded-up section 121 is, as mentioned above, less likely to open up because of creases mainly formed by the second embossing unit 63 or the like. This can definitely prevent the sideflap-folded-up section 121 from opening up as a result of separation of the temporarily-secured surfaces thereof due to air resistance in conveying, etc.

Figure 9:
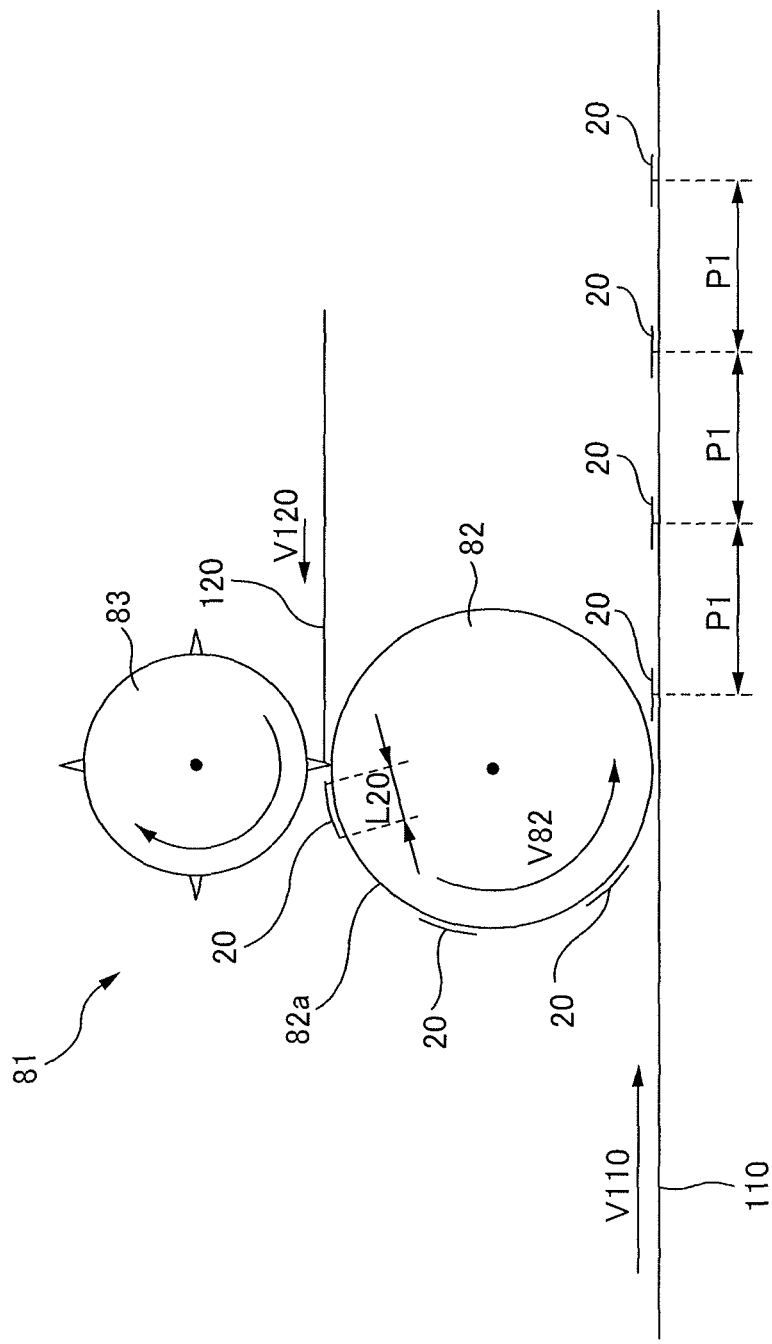
FIG. 9 is a schematic side view of an example of a second transfer device 81.

The configuration of the foregoing second transfer device 81 will be described briefly below. FIG. 9 is a schematic side view of one example of the second transfer device 81. The transfer device 81 includes a rotating drum 82 rotating at a peripheral speed V82 which is substantially the same as the conveying speed V110 of the continuous body 110 of the absorbent main body 10. On the outer circumferential surface 82a of the rotating drum 82, a sucking section which the band-member intermediate part 20 can be attached to or detached from is included. Further, a cutter roll 83 is placed facing the outer circumferential surface 82a.

The continuous sheet 120 associated with the band-member intermediate part 20 is transported toward the nip between the rotating drum 82 and the cutter roll 83, at the supply speed V120 which is slower than the peripheral speed V82 of the rotating drum 82. Therefore, that continuous sheet 120 is basically transported while sliding relatively in the reverse direction from the rotational direction of the outer circumferential surface 82a of the rotating drum 82. At the time when the continuous sheet 120 is transported by a corresponding amount to the length L20 of the band-member intermediate part 20, the front end section of the continuous sheet 120 is divided by the cutter roll 83. The divided front end section, which is the band-member intermediate part 20, is sucked and held by the outer circumferential surface 82a of the rotating drum 82, rotates together with the rotating drum 82, and is intermittently transported to the continuous body 110 of the absorbent main body 10 which is being conveyed while facing the outer circumferential surface 82a of the rotating drum 82. Finally, the front end section is joined to the same continuous body 110 with the product pitch P1.

===Other Embodiments===

While the embodiments according to the invention are described above, the invention is not limited to the embodiments and can be altered as described below.

In the description of the second embossing unit 63 in the foregoing embodiment, the configuration in which the embossing roll 64 and the anvil roll 65 for temporary-securing also serve as the pair of creasing rolls for creasing is provided as an example. However, this invention is not limited thereto. That is, a pair of an embossing roll and an anvil roll which perform temporary-securing may be different from a pair of creasing rolls which perform creasing. It should be noted that, in this case, a pair of creasing rolls may be a pair of rolls whose outer circumferential surface is smooth, for example.

In addition thereto, the pair of the embossing roll and the anvil roll and the pair of creasing rolls are placed adjacent to each other in the transporting direction of the continuous sheet 120. However, the sequence is not determined. That is, regardless of the sequence of the two steps, the temporary-securing and the creasing, there are advantages and disadvantages.

For example, if temporarily-securing the sideflap-folded-up section 121 prior to creasing, it is possible that when the pair of creasing rolls press the sideflap-folded-up section 121 the temporarily-secured surfaces of the sideflap-folded-up section 121 separate. On the other hand, in the case of creasing prior to temporarily-securing, it is possible that, when pressed by the embossing protrusions of the embossing roll, the surfaces which overlay in close contact with each other by creasing separate unintentionally, resulting in a gap between the surfaces.

Therefore, in order to avoid these problems, it is desirable that the embossing roll 64 and the anvil roll 65 which perform the temporary securing also function as the pair of creasing rolls, as mentioned above in the present embodiment. With such a configuration, the temporary securing by the embossing protrusion 66 and the creasing mainly by portion 67 surrounding the embossing protrusion 66 are both performed substantially simultaneously. Therefore, both the foregoing problems can be avoided; thereby, both of these steps can be performed reliably. Further, the number of rolls can be reduced in half, which results in simplifying the configuration of the apparatus or reducing costs.

In the foregoing embodiment, the embossing roll 54 and the anvil roll 55 of the first embossing unit 53 crimp the folded section 120b of the continuous sheet 120 with the embossing protrusions. However, this invention is not limited thereto. Further, it is possible to add to this first embossing unit 53 the configuration which is for creasing and is used in the second embossing unit 63. That is, in addition to the embossing protrusions of the embossing roll, the portion surrounding the embossing protrusion may press the folded section 120b co-operating with the smooth outer circumferential surface of the anvil roll. With such a configuration, either of the embossing protrusions and the portion surrounding the embossing protrusions constantly come into contact with and press the folded section 120b along the entire length thereof in the direction of the fold line L120b of the folded section 120b. This enables the folded section 120b to be fixed more firmly in a folded state.

In the foregoing embodiment, the band-member intermediate part 20 having the sideflap-folded-up section 121 is provided as an example of the sheet-like member including the folded-up sections which are temporarily secured in a folded-up state. However, this invention is not limited thereto. For example, the manufacturing method for a sheet-like member associated with the present embodiment may be applied to the manufacture of the urine-feces separating sheet of a disposable diaper.

A disposable diaper having this urine-feces separating sheet includes: a skin-side sheet which is in contact with the wearer's skin; and a surface sheet which is disposed closer to the absorbent body side than the skin-side sheet is and which covers the skin-side surface of the absorbent body. The skin-side sheet can separate from the surface sheet so that a proper space can be formed between these two sheets. Further, on the skin-side sheet, an opening for entrapping urine into the space and an opening for entrapping feces into the space are formed. Through these openings, the ejected feces or urine is entrapped into the space. Therefore, a configuration in which the ejected feces or urine is less likely to be in direct contact with the wearer's skin is realized.

However, it is possible that mixing of urine and feces in the space causes a chemical reaction. Therefore, in the space, the urine-feces separating sheet is placed; in addition, both end sections thereof are fixed respectively to the skin-side sheet and the surface sheet. In this way, the space is divided into two spaces, one for urine and the other for feces.

Herein, before the diaper is used, the skin-side sheet and the surface sheet are substantially in contact with each other and there is little space. On the other hand, during use, the skin-side sheet is separated from the surface sheet to form the space. Therefore, the urine-feces separating sheet is required to have a deformation capacity so that the space can expand and shrink. In this urine-feces separating sheet, the deformation capacity is realised by forming a folded-up section thereon. Further, because this folded-up section is temporarily secured in a folded-up state before the diaper is used, the manufacturing method associated with the present embodiment can be applied to the manufacture of such a urine-feces separating sheet.

REFERENCE SIGNS LIST 1 disposable diaper (absorbent article), 1a torso opening, 1b leg opening, 10 absorbent main body, 10a front end section, 10b rear end section, 11 absorbent body, 12 surface sheet, 13 back face sheet, 14 exterior sheet, 15 leakage-proof sheet, 16 elastic member, 17 standing-gather forming sheet, 20 band-member intermediate part (sheet-like member), 21 stomach-side band member, 21e first side flap, 25 back-side band member, 25e second side flap, 30 fastening member, 31 fastening tape, 31j connected body of fastening tape, 31je both end sections of connected body of fastening tape, 31m perforations, 32 tape substrate, 33 male component of hook-and-loop fastener, 37 target tape, 50 manufacturing apparatus, 51 first continuous-folding-plate device, 53 first embossing unit, 54 embossing roll, 55 anvil roll, 61 second continuous-folding-plate device (first unit), 63 second embossing unit (second unit, third unit), 64 embossing roll (pressing member, embossing roll, creasing roll), 65 anvil roll (roll, creasing roll), 66 embossing protrusion (protrusion), 67 portion surrounding embossing protrusion (portion surrounding protrusion), 71 first transfer device, 73 third embossing unit, 74 embossing roll, 75 anvil roll, 76 embossing protrusion, 77 portion surrounding embossing protrusion, 81 second transfer device (fourth unit), 82 rotating drum, 82a outer circumferential surface, 83 cutter roll, 110 continuous body of absorbent main body, 120 continuous sheet, 120b folded section, 120c central section, 120e end section 121 sideflap-folded-up section (folded-up section), 121b root section, 121e end section, A66 protrusion area (pressing region), AR remaining area, A76a protrusion area, A76b protrusion area, G66 embossing protrusion group (protrusion group), L120b fold line, L121 fold line, C54 rotational axis, C64 rotational axis, C74 rotational axis, BP1 boundary position

The invention claimed is:

1. A manufacturing method for a sheet-like member associated with an absorbent article, the sheet-like member having a folded-up section which is temporarily-secured in a folded-up state, comprising:
forming the folded-up section by folding up a continuous sheet in a width direction of the continuous sheet, the continuous sheet continuing along a transporting direction,
creasing the folded-up section in a folded-up state by pressing continuously the folded-up section along a direction of a fold line of the folded-up section,
temporarily-securing the folded-up section in a folded-up state by pressing the folded-up section with a plurality of protrusions that are included in a pressing member,
producing the sheet-like member by dividing the continuous sheet with a predetermined pitch in the transporting direction, the continuous sheet having been creased and temporarily-secured, and
conveying the produced sheet-like member, wherein
in the creasing,
in passing the continuous sheet through a nip between a pair of creasing rolls that rotate with their outer circumferential surfaces facing each other, the outer circumferential surface of the pair of creasing rolls continuously presses the folded-up section along the direction of the fold line,
in the temporarily-securing,
the pressing member includes
an embossing roll that rotates and has the plurality of protrusions on an outer circumferential surface thereof, and
a roll that rotates with an outer circumferential surface thereof facing the embossing roll, and
in passing the continuous sheet through a nip between the embossing roll and the roll, the protrusions and the outer circumferential surface press the folded-up section, the embossing roll and the roll also function as the pair of creasing rolls,
concerning creasing the folded-up section in a folded-up state, by constantly pressing the folded-up section with either of the protrusion of the embossing roll and a portion surrounding the protrusion, the folded-up section is continuously pressed along the direction of the fold line,
in the forming of the folded-up section, a pair of the folded-up sections are formed by folding up inwardly in the width direction both end sections of the continuous sheet in the width direction,
on the outer circumferential surface of the embossing roll, a protrusion group consisting of the plurality of protrusions is placed corresponding to the folded-up section,
in a cross-section taken perpendicular to a rotational axis of the embossing roll, the plurality of protrusions are arranged at a predetermined pitch around an entire circumference of the embossing roll,
the protrusion group is defined to have a predetermined width in a direction along the rotational axis of the embossing roll, and
the predetermined width of the protrusion group is set to be greater than a width of the folded-up section.

2. The manufacturing method according to claim 1, wherein
the outer circumferential surface of one of the pair of creasing rolls has a pressing region that presses the folded-up section, the pressing region is arranged around an entire circumference of the creasing roll in a cross-section taken perpendicular to a rotational axis of the creasing roll, the pressing region corresponding to the folded-up section and having a predetermined width in a direction along the rotational axis of the creasing roll, and
the predetermined width associated with the pressing region is set to be greater than a width of the folded-up section along the rotational axis of the creasing roll.

3. The manufacturing method according to claim 1, wherein
the continuous sheet is made mainly of a thermoplastic resin fiber, and
the outer circumferential surfaces of the pair of creasing rolls are heated by a heating device.

4. A method of manufacturing a sheet member associated with an absorbent article, the sheet member having a folded-up section which is temporarily-secured in a folded-up state, said method comprising:
forming the folded-up section by folding up a continuous sheet in a width direction of the continuous sheet, the continuous sheet continuing along a transporting direction, creasing the folded-up section in the folded-up state by pressing continuously the folded-up section along a direction of a fold line of the folded-up section, temporarily-securing the folded-up section in the folded-up state by pressing the folded-up section with a plurality of protrusions that are included in a pressing member, producing the sheet member by dividing the continuous sheet with a predetermined pitch in the transporting direction, the folded-up section of the continuous sheet having been creased and temporarily-secured, and
conveying the produced sheet member, wherein while being folded inwardly in the width direction, both end sections of the continuous sheet in the width direction are each fixed with an adhesive to form a pair of folded sections of the continuous sheet, in the forming, each pair of folded sections is folded up more inwardly in the width direction to form the folded-up section, the forming, the creasing, and the temporary-securing of the folded-up section are performed before the adhesive on the folded section loses its fluidity, in the forming of the folded-up section, a pair of the folded-up sections are formed by folding up inwardly in the width direction both end sections of the continuous sheet in the width direction, the outer circumferential surface of the embossing roll has a protrusion group consisting of the plurality of protrusions and placed corresponding to the folded-up section, in a cross-section taken perpendicular to a rotational axis of the embossing roll the plurality of protrusions are arranged at a predetermined pitch around an entire circumference of the embossing roll,
the protrusion group has a predetermined width in a direction along a rotational axis of the embossing roll, and
the predetermined width of the protrusion group is set to be greater than a width of the folded-up section.

5. The method according to claim 4, wherein
the outer circumferential surface of one of the pair of creasing rolls has a pressing region that presses the folded-up section, the pressing region is arranged around an entire circumference of the creasing roll in a cross-section taken perpendicular to a rotational axis of the creasing roll, the pressing region corresponding to the folded-up section and having a predetermined width in a direction along the rotational axis of the creasing roll, and the predetermined width associated with the pressing region is set to be greater than a width of the folded-up section along the rotational axis of the creasing roll.

6. The method according to claim 4, wherein the continuous sheet is made mainly of a thermoplastic resin fiber, and the outer circumferential surfaces of the pair of creasing rolls are heated by a heating device.

7. The method according to claim 4, wherein, in a cross-section taken perpendicular to the rotational axis of the embossing roll, the plurality of protrusions are arranged at a predetermined pitch around an entire circumference of the embossing roll.

8. A method of manufacturing a sheet member associated with an absorbent article, the sheet member having a folded-up section which is temporarily-secured in a folded-up state, said method comprising:

forming the folded-up section by folding up a continuous sheet in a width direction of the continuous sheet, the continuous sheet continuing along a transporting direction;

passing the continuous sheet through (i) a nip between a pair of creasing rolls that rotate with outer circumferential surfaces thereof, the outer circumferential surfaces of the pair of creasing rolls facing each other and (ii) a nip between an embossing roll and a roll, to crease and temporality secure the folded-up section in the folded-up state along the direction of the fold line of the folded-up section;

producing the sheet member by dividing the continuous sheet with a predetermined pitch in the transporting direction, the folded-up section of the continuous sheet having been creased and temporarily-secured; and conveying the produced sheet member, wherein the embossing roll rotates with an outer circumferential surface thereof, said outer circumferential surface of the embossing roll including a plurality of protrusions and a portion surrounding the plurality of protrusions, the roll rotates with an outer circumferential surface thereof facing the embossing roll, the folded-up section is continuously and constantly pressed, along the direction of the fold line of the folded-up section, by the plurality of protrusions of the embossing roll or by the portion surrounding the plurality of protrusion, to crease and temporarily-secure the folded-up section in the folded-up state, in the forming, a pair of the folded-up sections are formed by folding up inwardly in the width direction both end sections of the continuous sheet in the width direction, the outer circumferential surface of the embossing roll has a protrusion group consisting of the plurality of protrusions and placed corresponding to the folded-up section, in a cross-section taken perpendicular to a rotational axis of the embossing roll, the plurality of protrusions are arranged at a predetermined pitch around an entire circumference of the embossing roll, the protrusion group is defined to have a predetermined width in a direction along the rotational axis of the embossing roll, and the predetermined width of the protrusion group is set to be greater than a width of the folded-up section.

9. The method according to claim 8, wherein the outer circumferential surface of one of the pair of creasing rolls has a pressing region that presses the folded-up section, the pressing region is arranged around an entire circumference of the creasing roll in a cross-section taken perpendicular to a rotational axis of the creasing roll, the pressing region corresponding to the folded-up section and having a predetermined width in a direction along the rotational axis of the creasing roll, and the predetermined width associated with the pressing region is set to be greater than a width of the folded-up section along the rotational axis of the creasing roll.

10. The method according to claim 8, wherein the continuous sheet is made mainly of a thermoplastic resin fiber, and the outer circumferential surfaces of the pair of creasing rolls are heated by a heating device.

11. The method according to claim 8, wherein in the forming, while being folded inwardly in the width direction, the both end sections of the continuous sheet in the width direction are each fixed with an adhesive to form a pair of folded sections of the continuous sheet, and each of the pair of folded sections is folded up more inwardly in the width direction to form the folded-up section, and the folded-up section is creased and temporary-secured in the folded-up state along the direction of the fold line of the folded-up section before the adhesive on the folded section loses its fluidity.

* * * * *